(12) United States Patent
Miros

(10) Patent No.: US 6,871,878 B2
(45) Date of Patent: Mar. 29, 2005

(54) MAKE-BREAK CONNECTOR FOR HEAT EXCHANGER

(75) Inventor: Robert H. J. Miros, Mill Valley, CA (US)

(73) Assignee: Cool Systems, Inc., Berkeley, CA (US)

( * ) Notice: Subject to any disclaimer, the term of this patent is extended or adjusted under 35 U.S.C. 154(b) by 65 days.

(21) Appl. No.: 10/122,469

(22) Filed: Apr. 12, 2002

(65) Prior Publication Data

US 2003/0193188 A1 Oct. 16, 2003

(51) Int. Cl.$^7$ .......................... F16L 39/00; F16L 37/00
(52) U.S. Cl. .................... 285/124.5; 285/124.1; 285/124.2; 285/124.3; 285/124.4; 285/1; 285/308
(58) Field of Search .................. 285/308, 317, 285/1, 124.1, 124.2, 124.3, 124.4, 124.5; 137/594

(56) References Cited

U.S. PATENT DOCUMENTS

| | | | | |
|---|---|---|---|---|
| 2,510,125 A | * | 6/1950 | Meakin | 174/47 |
| 3,354,898 A | * | 11/1967 | Barnes | 137/331 |
| 4,116,476 A | * | 9/1978 | Porter et al. | 285/124.4 |
| 4,436,125 A | * | 3/1984 | Blenkush | 141/330 |
| 4,478,436 A | * | 10/1984 | Hashimoto | 285/124.4 |
| 4,753,268 A | * | 6/1988 | Palau | 137/595 |
| 5,201,552 A | * | 4/1993 | Hohmann et al. | 285/124.4 |
| 5,294,156 A | * | 3/1994 | Kumazaki et al. | 285/124.2 |
| 5,354,101 A | * | 10/1994 | Anderson, Jr. | 285/25 |
| 5,354,103 A | * | 10/1994 | Torrence et al. | 285/124.2 |
| 5,383,689 A | * | 1/1995 | Wolfe, Sr. | 285/124.3 |
| 5,556,138 A | * | 9/1996 | Nakajima et al. | 285/124.4 |
| 5,683,118 A | * | 11/1997 | Slocum | 285/119 |
| 5,920,934 A | * | 7/1999 | Hannagan et al. | 5/713 |
| 5,992,459 A | * | 11/1999 | Sugita et al. | 137/625.43 |
| 6,036,107 A | * | 3/2000 | Aspen et al. | 239/170 |
| 6,328,276 B1 | * | 12/2001 | Falch et al. | 251/54 |
| 6,354,635 B1 | * | 3/2002 | Dyson et al. | 285/308 |
| 6,382,678 B1 | * | 5/2002 | Field et al. | 285/3 |
| 6,443,498 B1 | * | 9/2002 | Liao | 285/124.1 |
| 6,547,284 B2 | * | 4/2003 | Rose et al. | 285/1 |

* cited by examiner

*Primary Examiner*—James M. Hewitt
(74) *Attorney, Agent, or Firm*—Michael B. Einschlag

(57) ABSTRACT

One embodiment of the present invention is a make-break connector for use, for example, with a heat exchanger, which make-break connector includes: (a) two or more connectors; and (b) a make-break mechanism affixed to one of the connectors.

23 Claims, 5 Drawing Sheets

MAKE-BREAK CONNECTOR FOR HEAT EXCHANGER

TECHNICAL FIELD OF THE INVENTION

One or more embodiments of the present invention pertain to a make-break connector for use, for example, and without limitation, with a heat exchanger.

BACKGROUND OF THE INVENTION

It is now common to apply cold and compression to a traumatized area of a human body to facilitate healing and prevent unwanted consequences of the trauma. Cold packing with ice bags or the like traditionally has been used to provide deep core cooling of a body part. Elastic wraps are often applied to provide compression. It will be appreciated that these traditional techniques are quite uncontrollable. For example, the temperature of an ice pack will, of course, change when the ice melts, and it has been shown that the application of elastic wraps and, consequently, the pressure provided by the same, varies considerably even where the wrappers are experienced individuals. Because of these and other difficulties, many in the field have turned to more complicated arrangements which include cooling units for maintaining a desired temperature through a splint or other heat exchanger. Some of these units also provide compressive pressure.

Prior art connectors that attach heat exchangers to a controller that supplies air flow and liquid flow are problematic. They are problematic because: (a) the connectors are not easily operated (i.e., the connections are not easily made or broken); (b) users cannot readily appreciate how to orient the connector for making the connection; and (c) a mistake in a user identifying a type of heat exchanger can cause it be connected to a controller that may, for example, supply too high a pressure for liquid and/or air flow and, thereby, raise safety issues.

In light of the above, there is a need in the art for a connector that solves one or more of the above-identified needs.

SUMMARY OF THE INVENTION

One or more embodiments of the present invention satisfy one or more of the above-identified needs in the art. In particular, one embodiment of the present invention is a make-break connector for use, for example, with a heat exchanger, which make-break connector comprises: (a) two more connectors; and (b) a make-break mechanism affixed to one of the connectors.

DETAILED DESCRIPTION

Figure 1:
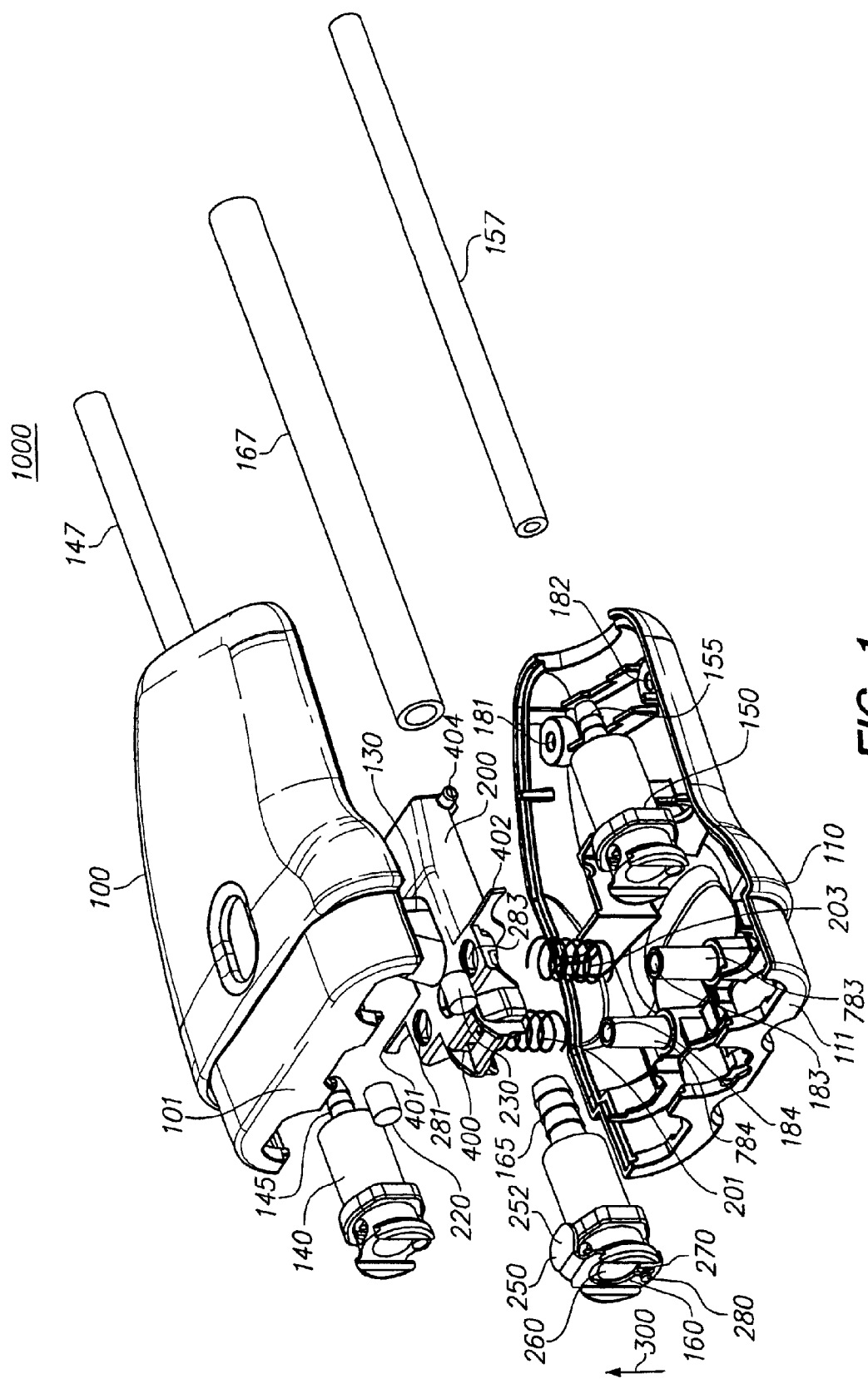
FIG. 1 shows an exploded view of a make-break connector that is fabricated in accordance with one embodiment of the present invention.

FIG. 1 shows an exploded view of make-break connector 1000 ("MBC 1000") that is fabricated in accordance with one embodiment of the present invention. MBC 1000 is adapted to interface to a heat exchanger, for example, and without limitation, a heat exchanger: (a) to which is flowed, for example, and without limitation, air and/or liquid (which air and/or liquid may be flowed, for example, under pressure), and (b) from which is flowed the liquid after circulation in the heat exchanger. One example of a heat exchanger that might utilize this embodiment of the present invention is a human body heat exchanger of a type comprising two overlapping bladders. In such a type of human body heat exchanger, a first bladder (for flow and distribution of a heat exchange liquid) is overlapped by a second bladder (for flow of air or some other gas to provide pressure for compression, and to assure good and intimate contact of the first bladder with a body part). Although air or some other gas could also be used in place of the heat exchange liquid, in most situations it is desirable to use a liquid because, among other reasons, of its thermal capacity.

As shown in FIG. 1, MBC 1000 comprises top shell housing 100 and bottom shell housing 110. Top shell housing 100 and bottom shell 110 housing are fabricated, for example, and without limitation, by molding high impact plastic such as polycarbonate plastic in accordance with any one of a number of methods that are well known to those of ordinary skill in the art (other suitable materials include various plastics and metals and combinations thereof). In accordance with one embodiment of the present invention, when top shell housing 100 and bottom shell housing 110 are assembled to form MBC 1000, a front surface of frontal portion 101 of top shell housing 100, and a front surface of frontal portion 111 of bottom shell housing 110 lie substantially in a plane. Further, frontal portions 101 and 111 have cutouts that support connectors 140, 150, and 160 in a manner to be described in detail below.

Figure 3:
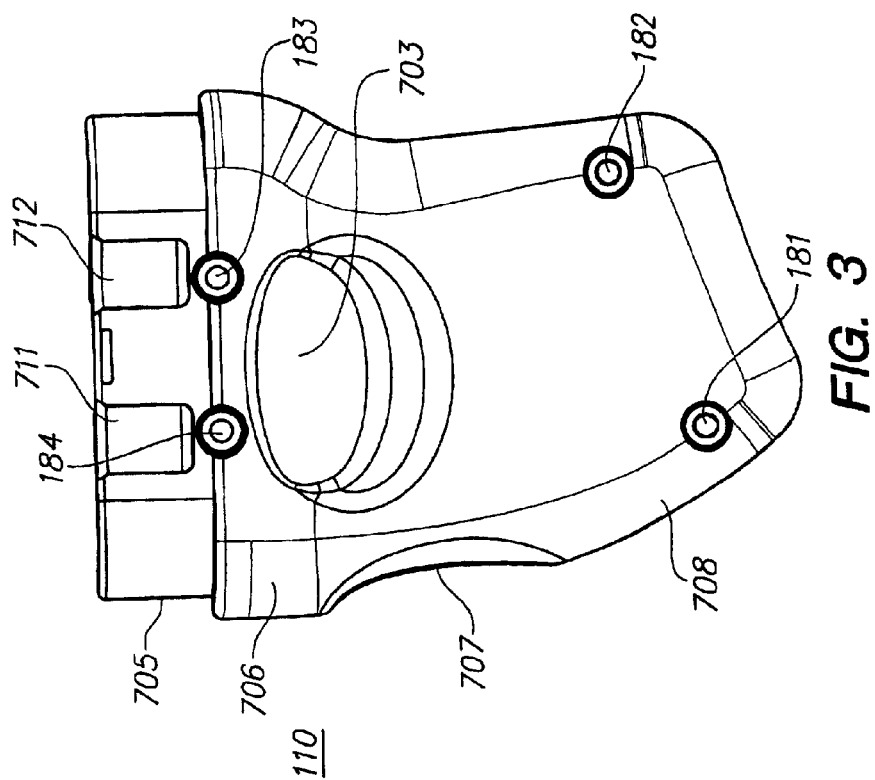
FIG. 3 shows a bottom view of the make-break connector shown in FIG. 1.
Figure 2:
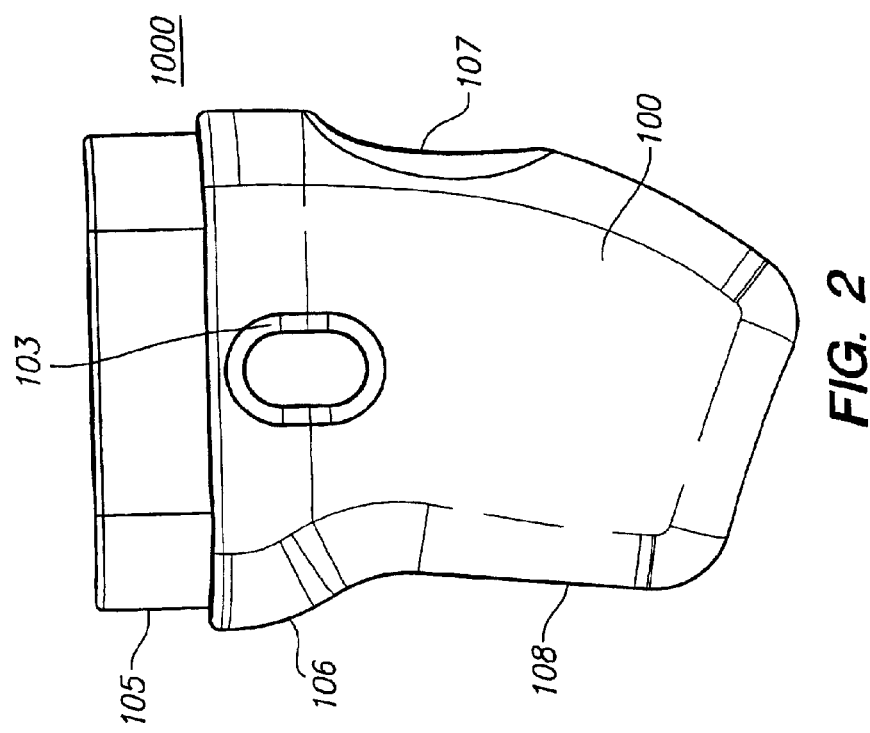
FIG. 2 shows a top view of the make-break connector shown in FIG. 1.

FIG. 2 shows a top view of MBC 1000 that illustrates a shape of the periphery of top shell housing 100, and FIG. 3 shows a bottom view of MBC 1000 that illustrates a shape of the periphery of bottom shell 110 housing. As shown in FIGS. 2 and 3, for one embodiment of the present invention, a profile of front portion 105 of top shell housing 100 is recessed from a profile of back portion 106 of top shell housing 100 (this feature can best be perceived by referring to a perspective view of top shell housing 110 shown in FIG. 5), and a profile of front portion 705 of bottom shell housing 110 is recessed from a profile of back portion 706 of bottom shell housing 110. As further shown in FIG. 3, for one embodiment of the present invention, front portion 705 of bottom shell housing 110 includes indentations 711 and 712 (this feature can best be perceived by referring to an end view of MBC 1000 shown in FIG. 4). In accordance with one or more such embodiments of the present invention, the recess in top shell housing 100 and bottom shell housing 110 enables a mating connector (for example, a mating connector that attaches to a control unit) to have a sleeve portion that fits over the front portions of top shell housing 100 and bottom shell housing 110 whenever the mating connector is mated with MBC 1000. Also, in accordance with one or more such embodiments of the present invention, indentations 711 and 712 may serve as guides and/or support mechanisms that are disposed in a sleeve portion of a mating connector.

As further shown in FIGS. 2 and 3, in accordance with one or more embodiments of the present invention, back portion 106 of top shell housing 100 and back portion 706 of bottom shell housing 110 have indented sections 107 and 707, respectively. Indented sections 107 and 707 provide a gripping area when a user holds MBC 1000. As still further shown in FIGS. 2 and 3, rear areas 108 and 708 of back portions 106 and 706, respectively, are curved or angled to a side; the arc of the curve or angle side flows away from indented sections 107 and 707, respectively. This feature enhances a user's ability to grip MBC 1000, and to hold it securely. As still further shown in FIG. 2, top shell housing 100 comprises hole area 103 through which button 130 (refer to FIG. 1) extends. Hole area 103 is substantially centrally located with respect to a width of front portion 105 of top shell housing 100. Lastly, as still further shown in FIG. 3, bottom shell housing 110 comprises recessed area 703 to enable a user more easily to grip MBC 1000. For example, in accordance with one such embodiment, recessed area 703 is located toward the front of bottom shell housing 110, and as such, provides a recess within which a user's index finger would reside to provide a good grip.

Figure 6:
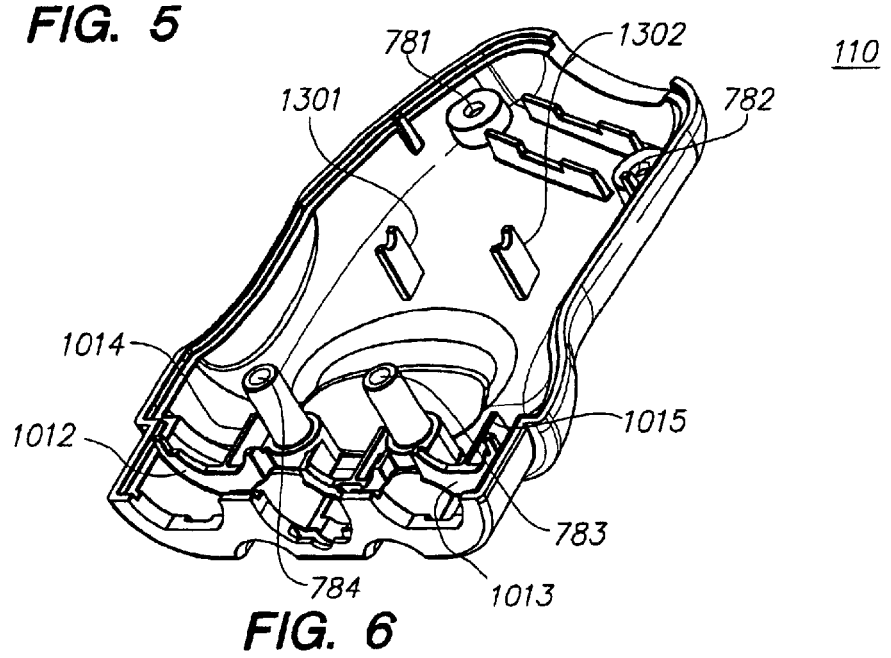
FIG. 6 shows a perspective view of an inside of a bottom shell housing of the make-break connector shown in FIG. 1.
Figure 7:
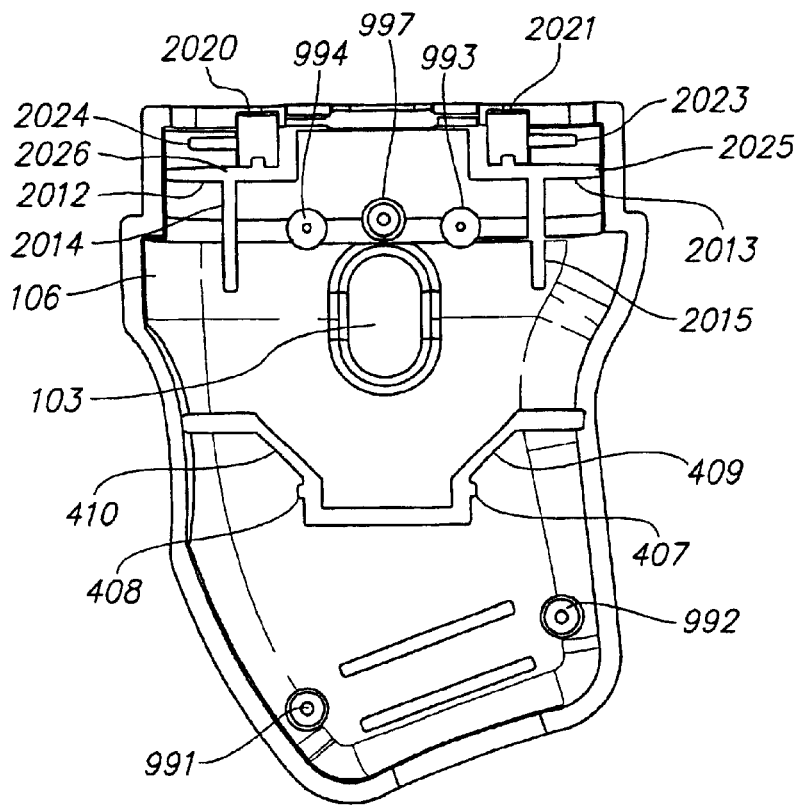
FIG. 7 shows a top view of an inside of the top shell housing of the make-break connector shown in FIG. 1.

As shown in FIGS. 1 and 6, bottom shell housing 110 includes bosses 781 and 782 disposed in the rear of back portion 706 (bosses 781 and 782 have passages 181 and 182 disposed therethrough—refer to FIG. 3), and bosses 783 and 784 disposed in the front of back portion 706 (bosses 783 and 784 have passages 183 and 184 disposed therethrough—refer to FIG. 3). In accordance with one embodiment, bosses 781–784 are fabricated integrally with bottom shell housing 110, and in another embodiment, they are affixed to bottom shell housing 110 by, for example, a fixative such as glue. As shown in FIG. 7, top shell housing 100 includes bosses 991 and 992 disposed in the rear of back portion 106 (bosses 991 and 992 have threaded holes disposed therein), and bosses 993 and 994 disposed in the front of back portion 106 (bosses 993 and 994 have threaded holes disposed therein). In accordance with one embodiment, bosses 991–992 are fabricated integrally with top shell housing 100, and in another embodiment, they are affixed to top shell housing 100 by, for example, a fixative such as glue. When MBC 1000 is assembled, screws (not shown) are inserted through passages 181–184 in bottom shell housing 110, and are threaded into bosses 991–994 disposed on top shell housing 100.

In accordance with one embodiment, the heights of bosses 781–782 and 991–992 are such that bosses 781–782 substantially kiss-off, or mate with, bosses 991–992, respectively, whenever the screws are inserted and tightened, thereby providing structural support for MBC 1000. In addition, as can be understood from FIG. 1, bosses 993 and 994 have a predetermined height which is sufficient to support springs 201 and 203 of make-break mechanism 200 ("MBM 200") whenever MBC 1000 is assembled. In accordance with one such embodiment, the height of bosses 783–784 on bottom shell housing 110 and the height of bosses 993 and 994 on top shell housing 100 are such that bosses 783–784 do not kiss-off bosses 993–994, respectively, whenever the screws are inserted and tightened. Lastly, bosses 993–994 on top shell housing 100 also serve as an anchoring mechanism (in a manner to be described in detail below) for MBM 200 when MBC 1000 is assembled.

As shown in FIG. 1, MBC 1000 comprises connectors 140 and 150 which comprise hose barbs 145 and 155, respectively (for example, and without limitation, ⅛" hose barbs). In accordance with one embodiment of the present invention, connectors 140 and 150 are designed: (a) to connect (at a front end) to a control unit that supplies fluid under pressure to one of connectors 140 and 150; and (b) to connect (at a back end) to a heat exchanger that supplies fluid to the other one of connectors 140 and 150. In accordance with such an embodiment, hose barbs 145 and 155 connect to tubes 147 and 157 shown in FIG. 1, respectively (for example, and without limitation, tubes 147 and 157 may be ⅛" ID polyurethane tubes).

Figure 4:
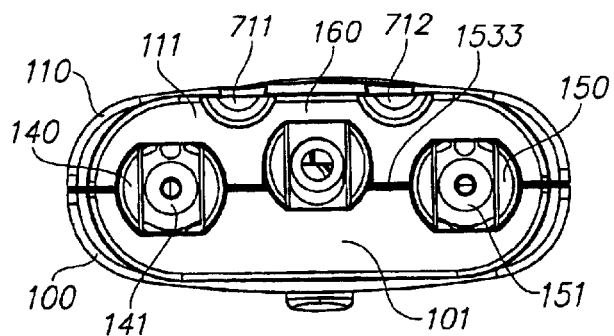
FIG. 4 shows an end view of the make-break connector shown in FIG.
Figure 5:
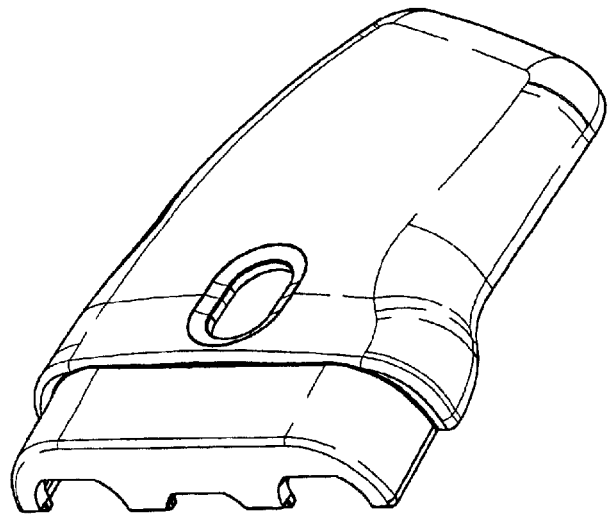
FIG. 5 shows a perspective view of a top shell housing of the make-break connector shown in FIG. 1.
Figure 10:
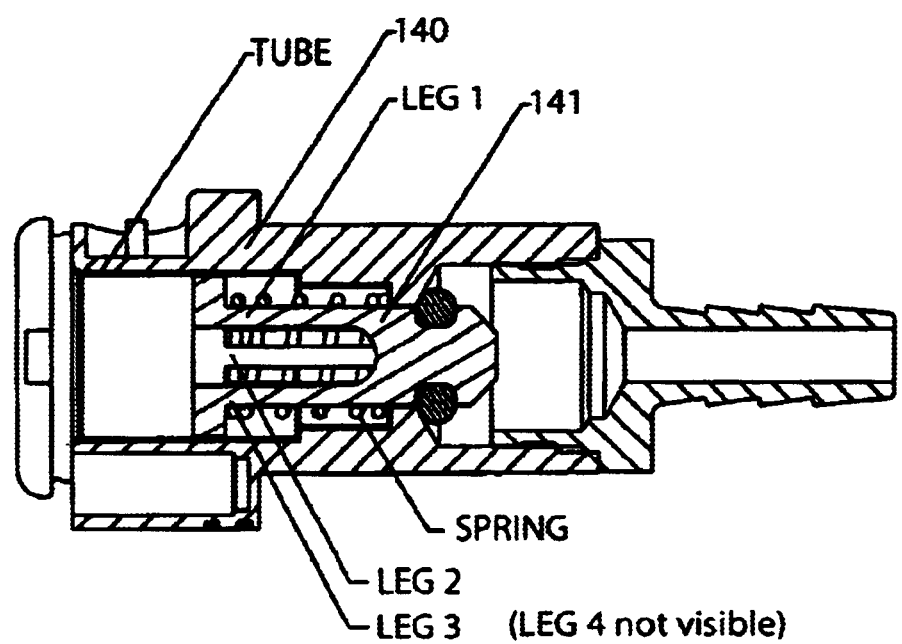
FIG. 10 shows a cross section of a valved connector used to fabricate one or more embodiments of the present invention.

In accordance with one embodiment of the present invention, connectors 140 and 150 are valved or self-closing connectors that are commercially available, for example, from Colder Products Inc. of Minneapolis, Minn. FIG. 4 shows an end view of MBC 1000 for an embodiment wherein connector 140 and connector 150 are the same device. Despite this, those of ordinary skill in the art should appreciate that the present invention is not limited to embodiments wherein connectors 140 and 150 are the same device. In fact, further embodiments exist wherein connector 140 and connector 150 are different devices, including embodiments wherein one and/or the other is unvalved or valved, as the case may be. FIG. 10 shows a cross section of connector 140 that may be used to fabricate one or more embodiments of the present invention. (As also shown in FIG. 4, in one embodiment where connector 140 comprises a commercially available valved connector, connector 140 includes structure 141 that is disposed in a tube within connector 140). As shown in FIG. 10, the tube extends for a predetermined distance (from a front surface of the connector) into connector 140 to a valve. In accordance with one such embodiment, a front portion of structure 141 is formed from a sheet of plastic material having a substantially planar front surface, an aperture disposed substantially in a center of the sheet, and four (4) legs radially disposed about the aperture so that the legs support the front portion by reaching the walls of the tube as structure 141 moves in and out of the tube. As further shown in FIG. 10, the leg structure is affixed to a back surface of the front portion of structure 141, which leg structure is surrounded by a spring. The spring biases structure 141 (and thereby its leg structure) toward the front of connectors 140, but some distance back from the front surface of connector 140. Structure 141, and its associated leg structure, are adapted to move back and forth in the tube of connector 140. In accordance with one such embodiment of the present invention, connector 150 includes structure 151 that operates, and is constructed in the same manner as structure 141.

To make a connection with MBC 1000, male connecting extensions of the mating connector are inserted into the tubes in connectors 140 and 150, and the male connecting extensions press against the front portions of structures 141 and 151 of connectors 140 and 150, respectively. The male connecting extensions drive structures 141 and 151 (and hence their leg structures) into connectors 140 and 150, respectively. The length of the leg structures is chosen to be long enough so that when the leg structures are driven as far as they can be driven by insertion of the male connecting extensions into the tubes in connectors 140 and 150, there is substantially no play in the direction of insertion (for example, and without limitation, the back of the leg structures may hit a stop, and cannot be moved further in a direction into connectors 140 and 150). In this position, movement of the leg structures causes valves to open. Further, the depth of insertion of the male connecting extensions ought to be such that when the male connecting extensions have been fully inserted into connectors 140 and 150, a front surface of the mating connector is substantially aligned against a front surface of connector 140 and connector 150.

As one can readily appreciate from the above, whenever the male connecting extensions are inserted into the tubes in connectors 140 and 150, and the male connecting extensions move structures 141 and 151 into their respective tubes, the springs disposed about the leg structures are compressed. Compression of the springs provides forces that resist further insertion. In accordance with one embodiment of the present invention, the springs have high enough tension so that upon disconnect (i.e., an activation of MBM 200 that releases a lock holding the mating connector in a connection position), the springs drive structures 141 and 151 (and hence their leg structures) toward the front surfaces of connectors 140 and 150 so rapidly that the valves are open for so short a time that substantially no fluid leaks. As one can readily appreciate from the above, in accordance with this embodiment of the present invention, connectors 140 and 150 do not hold onto the mating connector.

As shown in FIGS. 1 and 4–6, bottom shell housing 110 includes cutouts in frontal portion 111 that support connectors 140 and 150, and top shell housing 100 includes cutouts in frontal portion 101 that support connectors 140 and 150. As seen in FIG. 4, in accordance with one embodiment, a bottom of each cutout is a substantially straight line, and the sides of each cutout are arcs of, for example, a circle. In addition, in accordance with one or more embodiments of the present invention, top shell 100 and bottom shell 110 include further structure for supporting connectors 140 and 150. It should be appreciated that embodiments of the present invention are not limited to those having cutouts of the type disclosed in FIGS. 1 and 4–6. In fact, further embodiments exist wherein cutouts having further shapes are utilized.

As shown in FIGS. 6 and 7, in accordance with one embodiment of the present invention, top shell housing 100 and bottom shell housing 110 include further structure to provide support for connectors 140 and 150. In particular, such further structure includes: (a) first ribs 1012 and 1013 of bottom shell housing 110 that lie in a plane that is substantially parallel to the front surface of frontal portion 111 of bottom shell housing 110; and (b) first ribs 2012 and 2013 of top shell housing 100 that lie in a plane that is substantially parallel to the front surface of frontal portion 101 of top shell housing 110. In addition, in accordance with one embodiment of the present invention, the further structure also includes: (a) second ribs 1014 and 1015 of bottom shell housing 110 that lie in planes that are substantially perpendicular to the front surface of frontal portion 111 of bottom shell housing 110, which second ribs 1014 and 1015 provide structural support for first ribs 1012 and 1013, respectively; and (b) second ribs 2014 and 2015 of top shell housing 100 that lie in planes that are substantially perpendicular to the front surface of frontal portion 101 of top shell housing 100, which second ribs 2014 and 2015 provide structural support for first ribs 2012 and 2013, respectively. In accordance with one embodiment of the present invention, the further structures are fabricated integrally with top shell housing 100 and bottom shell housing 110, respectively, and in accordance with another embodiment, they are affixed to top shell housing 100 and bottom shell housing 110 by, for example, a fixative such as glue.

As shown in FIG. 7, top shell housing 100 includes wells 2020 and 2021 that are disposed between frontal portion 101 and ribs 2012 and 2013, respectively. In accordance with one embodiment of the present invention, wells 2020 and 2021 are in the shape of a half-cylinder whose axis is substantially perpendicular to the front surface of frontal portion 101. In accordance with one embodiment of the present invention, one end surface of wells 2020 and 2021 is embedded in frontal portion 101, and the other end surface of wells 2020 and 2021 abut ribs 2025 and 2026. Lastly, ribs 2023 and 2024 abut transverse sides of wells 2020 and 2021, respectively. One or both of magnets 220 and 230 (shown in FIG. 1) may be placed in wells 2020–2021. Then, when MBC 1000 is assembled, magnet 220 and/or magnet 230 are held in place in wells 2020–2021 by the surfaces of wells 2020–2021, ribs 2023, 2024 and 2025, 2026, respectively, and by a periphery of connectors 140 and 150, respectively. It should be appreciated that embodiments of the present invention are not limited to those having wells of the shape described above. In fact, further embodiments exist wherein wells having further shapes are used, and still further embodiments exist where magnets are disposed in alternative locations. In accordance with one embodiment of the present invention, a portion of the front surface of connector 140 and/or connector 150 is recessed so that a portion of a front surface of magnet 220 and/or magnet 230 is exposed to enable the magnetic field to extend a predetermined distance from MBC 1000.

In accordance with one embodiment of the present invention, magnets 220 and 230 are neodymium permanent magnets, and at least portions thereof are visible when MBC 1000 is assembled. Magnets 220 and 230 may be used to identify a particular type of heat exchanger for identification and safety. For example, in accordance with one embodiment of the present invention, a mating connector includes a sensing mechanism, for example, and without limitation, a magnetic reed switch. If one of magnets 220 and 230 is included in MBC 1000, this may serve to identify one type of heat exchanger. If both of magnets 220 and 230 are included in MBC 1000, this may serve to identify another type of heat exchanger. The identities of the type of heat exchanger to which it is connected may be used by a control unit to control one or more parameters sets. For example, among other things, the control unit may use the identity to control the pressure of the liquid supplied to the heat exchanger through MBC 1000. In some embodiments it may be desirable to distinguish between more than two heat exchangers. Such an embodiment can be implemented by utilizing more magnets, and/or by utilizing different polarities of magnets and detectors for the same. In this connection, it should be noted that switches are available that are sensitive to magnetic polarity. It should be understood that further embodiments of the present invention may be fabricated using a greater number of magnets. Still further embodiments may be fabricated wherein the magnets are disposed so as to hidden from view when MBC 1000 is assembled. Yet still further embodiments may be fabricated wherein the strength of the magnets is increased (by use of stronger magnets), and the placement can be further from detectors in the mating connector (for example, further than about ¼").

As shown in FIG. 1, MBC 1000 comprises connector 160. Connector 160 comprises hose barb 165 (for example, and without limitation, a ¼" hose barb). In accordance with one embodiment of the present invention connector 160 is designed: (a) to connect, at a front end, to a control unit that supplies air under pressure to connector 160; and (b) to connect, at a back end, to a heat exchanger. In accordance with such an embodiment, hose barb 165 connects to tube 167 (for example, and without limitation, tube 167 may be a ¼" ID polyurethane tube). Connector 160 interfaces with MBM 200 in a manner that will be described in detail below.

As shown in FIG. 4, in accordance with one embodiment of the present invention, centers of connectors 140 and 150 lie substantially along line 1533 where top shell housing 100 joins bottom shell housing 110 when MBC 1000 is assembled. In accordance with one embodiment of the present invention, the centers are spaced apart by as much as about 22.4 mm. However, further embodiments can be fabricated wherein the spacing between the centers is different from this. For example, the spacing can vary in a range from about 15 mm to about 60 mm for a connector that can comfortably fit in an average person's hand. As further shown in FIG. 3, a center of connector 160 is displaced in a direction that is perpendicular to line 1533. In accordance with one embodiment of the present invention, the center of connector 160 is spaced a distance of about 3.3 mm from line 1533. As shown in FIG. 3, the center of connector 160 is displaced away from top shell housing 100. However, further embodiments may be fabricated where there is no displacement of the center of connector 160, or still further embodiments in which the displacement is towards top shell housing 100. For example, the displacement can vary in a range from about 0 mm to about 10 mm for a connector that can comfortably fit in an average person's hand. It has been discovered that displacing the center of connector 160 better enables a user to distinguish the proper side of MBC 1000 to use in orienting it for connection.

As shown in FIG. 4, at least portions of front faces of connectors 140, 150, and 160 lie substantially in a plane that includes front surfaces of frontal portion 101 of top shell housing 100 and frontal portion 111 of bottom shell housing 110. As was described above, frontal portions 101 and 111 include cutouts that are substantially in the shape of a periphery of the front faces of connectors 140, 150, and 160. However, in accordance with one embodiment of the present invention, the cutouts in frontal portions 101 and 111 corresponding to connector 160 are so close to the same size as the periphery of connector 160 that connector 160 is substantially tightly contained at a predetermined position in the plane that includes the front surfaces of frontal portion 101 and frontal portion 111 of top shell housing 100 and bottom shell housing 110, respectively. Such an embodiment is useful in aligning the mating connector for an air line. By contrast, in one such embodiment, the cutouts in frontal portions 101 and 111 corresponding to connectors 140 and 150 are larger in size than the periphery of connectors 140 and 150 so that connectors 140 and 150 are not tightly constrained to predetermined positions in the plane that includes the front surfaces of frontal portion 101 and frontal portion 111 of top shell housing 100 and bottom shell housing 110, respectively. It has been found that providing space for connectors 140 and 150 to move about predetermined positions in the plane better enables a user to align a mating connector with MBC 1000. Finally, in accordance with one embodiment of the present invention, connectors 140, 150, and 160 are all held to a reasonably tight tolerance in a direction perpendicular to the plane (i.e., along a direction into or out of top shell housing 100 and bottom shell housing 110).

In accordance with one embodiment of the present invention, connector 160 is a connector that is not valved or self-closing, and which is commercially available, for example, from Colder Products Inc. of Minneapolis, Minn. As shown in FIG. 1, latch structure 250 (fabricated, for example, from metal) is inserted into slots disposed in a frontal portion of connector 160, and which slots are disposed on either side of aperture 260 (for example, a circular, central aperture) of connector 160. As further shown in FIG. 1, latch structure 250 also has an aperture, for example, a circular, central aperture, whose diameter is substantially the same as the diameter of aperture 260 at a front end of connector 160. As still further shown in FIG. 1, latch structure 250 includes slot 270 through which pin 280 protrudes. Pin 280 rides in a channel in connector 160 along a direction into and out of connector 160. Pin 280 is biased by a spring (not shown) that is located in the channel, which spring is attached to a support at a bottom of the channel. Further, pin 280 has a groove which circles pin 280, which groove is located a predetermined distance from an end of pin 280.

To understand how latch structure 250 operates, assume that latch structure 250 is urged along a direction opposite to arrow 300 of FIG. 1 when button 130 is pressed by a user (the mechanism that urges latch structure 250 in this manner will be described in detail below). This releases pin 280 so that it is urged by the spring to extend so far out from the channel that the location of the groove in pin 280 extends beyond latch structure 250. When button 130 is released, latch structure 250 is urged along the direction of arrow 300 (the mechanism that urges latch structure 250 in this manner will be described in detail below). As a result, slot 270 of latch structure 250 will surround pin 280 at its periphery (but outside the groove). In this position, due to the radius of the periphery of pin 280, latch structure 250 is positioned so that the aperture in latch structure 250 and aperture 260 in connector 160 are coincident. Whenever this occurs, the aperture in latch structure 250 and aperture 260 in connector 160 allow a male connecting extension of a male connector to be inserted into connector 160. In accordance with one embodiment of the present invention, a structure (not shown) through which air may pass, for example, a cross, is disposed at a predetermined depth inside aperture 260 to provide a stop for insertion of the male connecting extension. The depth of insertion of the male connecting extension ought to be such that when the male connecting extension is fully inserted into connector 160, the mating connector substantially abuts a front surface of connector 160. As one can readily appreciate, as it is being inserted, a surface of the mating connector will engage pin 280, which (for the case where the aperture in latch structure 250 coincides with aperture 260 in connector 160) extends beyond the front surface of connector 160. Then, as the mating connector is further inserted, it urges pin 280 into the channel. Note that latch structure 250 is being urged (in a manner that will be described below) along the direction of arrow 300. Whenever pin 280 is moved by the surface of the mating connector to a position where the groove is lined up with latch structure 250, latch structure 250 is able to move so that slot 270 surrounds pin 280 at the groove. In this position, pin 280 holds latch structure 250 in a position so that an edge of the aperture in latch structure 250 is inserted into a slot, for example, in the male connecting extension. In this position, the mating connector is connected to MBC 1000.

Figure 8:
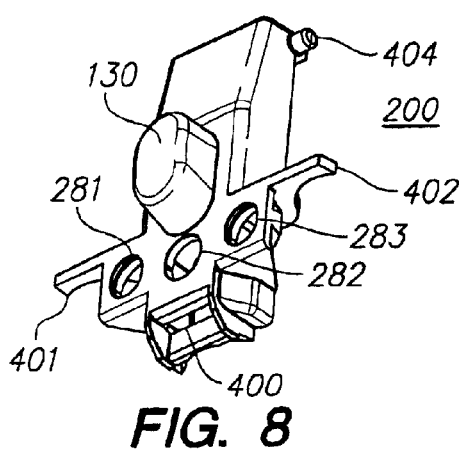
FIG. 8 shows a perspective view of a make-break mechanism of the make-break connector shown in FIG. 1.
Figure 9:
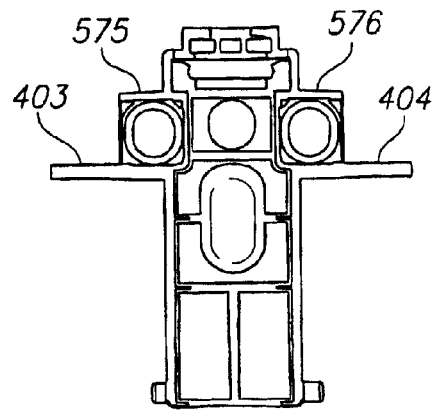
FIG. 9 shows a bottom view of a bottom of the make-break mechanism of the make-break connector shown in FIG. 1.

As shown in FIG. 8, in accordance with one embodiment of the present invention, MBM 200 includes button 130, setting holes 281–283, wings 401–402, pegs 403–404 (also see FIG. 9), and slot 400. In accordance with this embodiment, when MBC 1000 is assembled: (a) button 130 protrudes through hole area 103 in top shell housing 100; (b) setting holes 281 and 283 surround bosses 994 and 993, respectively, of top shell housing 100; (c) setting hole 282 surrounds boss 997 of top shell housing 100 to provide a measure of support for MBM 200; (d) wings 401–402 are disposed to land on an inner surface of top shell housing 100 and to provide a measure of support for MBM 200 when springs 201 and 203 urge MBM 200 against the inner surface; (e) pegs 403–404 are held in grooves 407–408 in ribs 409–410 (see FIG. 7) to provide a pivot point for rotation of MBM 200 when button 130 is depressed and MBM 200 is rotated into MBC 1000 away from top shell housing 100 (as shown in FIG. 6, ribs 1301 and 1302 in bottom shell housing 110 include grooves to hold pegs 403–404 in place in grooves 407–408 when MBC 1000 is assembled); and (f) slot 400 in MBM 200 holds tab 252 of latch structure 250. Springs 201 and 203 sit in wells 575 and 576 that surround holes 281 and 283, respectively (refer to FIG. 9). In addition, springs 201 and 203 surround bosses 784 and 783, respectively, of bottom shell housing 110. In operation, springs 201 and 203 urge MBM 200 along a direction shown by arrow 300 relative to connector 160 (connector 160 is held relatively rigidly by the cutouts in top shell housing 100 and bottom shell housing 110). As a result, since tab 252 of latch structure 250 is held by MBM 200, springs 201 and 203 also urge latch structure 250 along the direction shown by arrow 300. By pressing button 130, latch structure 250 is moved in the opposite direction.

Lastly, as shown in FIGS. 6 and 7, top shell housing 100 and bottom shell housing 110 include openings (in the rear of each) and ribs (disposed toward the rear of each) to aid in distributing tubes 147, 157, and 167.

Although various embodiments that incorporate the teachings of the present invention have been shown and described in detail herein, those skilled in the art can readily devise many other varied embodiments that still incorporate these teachings.

What is claimed is:

1. A make-break connector that comprises:
   two or more connectors, each of which two or more connectors is adapted to be connected at a first end to a first conduit and at a second end to a second conduit, wherein one of the connectors is a locking connector having an insertion channel therein with an insertion aperture;
   a housing having a frontal portion that has: (a) a front surface disposed in a front surface plane and (b) cutouts that support the connectors so that at least portions of front faces of the connectors are disposed in the front surface plane;
   a make-break mechanism disposed in the housing that includes a button mechanism and a spring mechanism that biases the make-break mechanism so that at least a portion of the button mechanism extends through an aperture in the housing;
   a latch structure that is affixed to the locking connector wherein the latch structure includes a tab which tab is connected to the make-break mechanism so that: (a) when the button mechanism is pushed, the latch structure is driven in a first direction, and (b) when the button mechanism is released, the spring mechanism urges the make-break mechanism so that the latch structure is driven in a second direction which is opposite the first direction;
   wherein the latch structure has: (a) an aperture whose shape and area is substantially the same as a shape and area of the insertion aperture, and (b) a slot; and
   a pin that: (a) rides in a pin channel in the locking connector, which pin channel disposed along a direction into and out of the locking connector, (b) is biased by a pin spring toward a front of the pin channel, (c) has a groove located a predetermined distance from an end of the pin;
   whereby: (a) when the latch structure is driven in the first direction, the pin is releases and the pin spring urges the pin so the groove extends beyond the slot; (b) when the latch structure is driven in the second direction, the slot surrounds the pin outside the groove and the aperture in the latch structure and the aperture in the locking connector are coincident, allowing a male connecting extension of a mating connector to be inserted into the insertion channel, wherein the mating connector engages the pin as it extends beyond a front surface of the locking connector and urges the pin into the pin channel, and when the groove is lined up with the latch structure, the latch structure is able to move so the slot surrounds the pin at the groove, and so that an edge of the aperture in the latch sturcture inserted into a slot in the mating connector.

2. The make-break connector of claim 1 wherein one or more of the connectors is valved.

3. The make-break connector of claim 1 wherein the locking connector is unvalved.

4. The make-break connector of claim 1 wherein: (a) the housing includes wells that are disposed behind the front surface of the frontal portion; and (b) one or more magnets disposed in the wells so that a magnetic field extends from the one or more magnets a predetermined distance from the make-break connector.

5. The make-break connector of claim 4, wherein one magnet identifies a first type of apparatus is to be connected to the make-break connector and a larger number of magnets identifies that other types of apparatus are to be connected to the make-break connector.

6. The make-break connector of claim 4 wherein the one or more magnets are neodymium permanent magnets.

7. The make-break connector of claim 4 which further comprises a mating connector that includes a magnetic reed switch.

8. The make-break connector of claim 7 wherein the magnetic field sensing mechanism includes a magnetic reed switch.

9. The make-break connector of claim 1 wherein the two or more connectors comprise two connectors in addition to the locking connector and wherein a center of the two additional connectors that are spaced apart by a distance in a range from about 20 mm to about 60 mm.

10. The make-break connector of claim 9 wherein a center of the locking connector is disposed between the two additional connectors and is displaced in a direction that is perpendicular to a line joining the centers of the two additional connectors.

11. The make-break connector of claim 1 wherein: (a) the cutouts are substantially in a shape of a periphery of front faces of the connectors; (b) the cutout that supports the locking connector is configured so the locking connector is fixed in the front surface plane; and (c) the cutouts that support the other connectors are configured so the other connectors can move within the front surface plane.

12. The make-break connector of claim 1 wherein: (a) at least one of the connectors is a valved connector; (b) the at least one of the connectors includes a male reception structure disposed and movable within a tube in the at least one of the connectors, which tube extends a predetermined distance from a front of the at least one of the connectors to a valve; and (c) the male reception structure includes a front reception portion having an aperture and a spring mechanism that biases the male reception structure toward a front of the tube at a predetermined distance back from the front of the at least one of the connectors so that the male reception structure is pushed into the tube and the spring mechanism is compressed when a male connecting extension of a mating connector is inserted into the tube.

13. The make-break connector of claim 12 wherein the spring mechanism of the male reception structure has a sufficiently large spring coefficient so that the spring mechanism can drive the male reception structure toward the front of the valved connector so rapidly that the valve is opened for so short a time that there is substantially no leak.

14. The make-break connector of claim 12 wherein the male reception structure includes a leg structure extending into the tube from the front reception portion which is long enough so that when the leg structure is driven by insertion of the male connecting extension into the tube a back of the leg structure causes the valve to open; and a depth of insertion of the male connecting extension is such that when the male connecting extension has been fully inserted into the valved connector, a front surface of the mating connector is substantially aligned against the front surface of the valved connector.

15. The make-break connector of claim 1 wherein one or more of the connectors includes a hose barb at the second end.

16. The make-break connector of claim 1 wherein each of the connectors is adapted to receive a male connecting extension of a mating connector.

17. The make-break connector of claim 1 wherein a profile of the frontal portion of the housing is recessed from a profile of a back portion of the housing to a depth sufficient to enable a sleeve portion of a mating connector to fit over the frontal portion whenever the mating connector is connected to the make-break connector.

18. The make-break connector of claim 1 wherein the frontal portion of the housing includes one or more indentations that serve as guides and/or support mechanisms for structure disposed in a sleeve portion of a mating connector.

19. The make-break connector of claim 1 wherein: (a) a back portion of the housing has indented gripping sections; (b) a rear area of the back portion of the housing is angled to a side, and the arc of the angle flows away from the indented gripping sections; and (c) the housing has a recessed area which is located toward a front of the housing.

20. The make-break connector of claim 1 wherein: (a) bosses are disposed in a front of a back portion of the housing and are disposed through apertures in the make-break mechanism so that the make-break mechanism can ride up and down the bosses; and (b) the bosses support the spring mechanism that biases the make-break mechanism.

21. The make-break connector of claim 1 wherein the latch structure inserted into slots disposed in a frontal portion of the locking connector, which slots are disposed on either side of the insertion aperture of the locking connector.

22. The make-break connector of claim 1 wherein the tab is inserted into a slot in the make-break mechanism.

23. The make-break connector of claim 1 wherein a structure is disposed at a predetermined depth inside the locking connector to provide a stop for insertion of a male connecting extension of a male connector, and a depth of insertion of the male connecting extension is such that, when the male connecting extension is fully inserted into the locking connector, the mating connector substantially abuts a front surface of the locking connector.

* * * * *